US00PP20651P2

(12) United States Plant Patent
Kraan

(10) Patent No.: US PP20,651 P2
(45) Date of Patent: Jan. 19, 2010

(54) ***ROSA* PLANT NAMED 'BOKRAMMI'**

(50) Latin Name: *Rosa hybrida*
Varietal Denomination: Bokrammi

(75) Inventor: Kees Jan Kraan, Papenveer (NL)

(73) Assignee: Boot & Co. Boonkwekerijen B.V., Boskoop (NL)

( * ) Notice: Subject to any disclaimer, the term of this patent is extended or adjusted under 35 U.S.C. 154(b) by 0 days.

(21) Appl. No.: 12/228,291

(22) Filed: Aug. 11, 2008

(51) Int. Cl.
*A01H 5/00* (2006.01)

(52) U.S. Cl. ..... Plt./130

(58) Field of Classification Search ..... Plt./130
See application file for complete search history.

(56) References Cited

OTHER PUBLICATIONS

Upov Plant Variety Database 2009/02 p. 1.*

* cited by examiner

*Primary Examiner*—Annette H Para
(74) *Attorney, Agent, or Firm*—C. A. Whealy

(57) ABSTRACT

A new and distinct cultivar of Rose plant named 'Bokrammi', characterized by its upright and mounding plant habit; dark green-colored foliage; freely branching growth habit; freely flowering habit; red purple-colored flowers; large glossy red-colored fruits; and good garden performance.

1 Drawing Sheet

Botanical designation: *Rosa hybrida.*
Cultivar denomination: 'Bokrammi'.

BACKGROUND OF THE INVENTION

The present Invention relates to a new and distinct cultivar of Rose plant, botanically known as *Rosa hybrida,* commercially used as an ornamental shrub, and hereinafter referred to by the name 'Bokrammi'.

The new Rose plant is a product of a planned breeding program conducted by the Inventor in Boskoop, The Netherlands. The objective of the breeding program was to develop new uniform shrub Rose varieties with attractive flower and fruit coloration.

The new Rose plant originated from a cross-pollination made by the Inventor during the summer of 1996 of two unnamed seedling selections of *Rosa hybrida,* not patented. The new Rose plant was discovered and selected by the Inventor during the summer of 2001 as a single flowering plant within the progeny of the stated cross-pollination in a controlled outdoor nursery environment in Boskoop, The Netherlands.

Asexual reproduction of the new Rose plant by softwood cuttings in a controlled greenhouse environment in Boskoop, The Netherlands since the summer of 2001, has shown that the unique features of this new Rose plant are stable and reproduced true to type in successive generations of asexual reproduction.

SUMMARY OF THE INVENTION

The following traits have been repeatedly observed and are determined to be the unique characteristics of 'Bokrammi'. These characteristics in combination distinguish 'Bokrammi' as a new and distinct cultivar of Rose:

1. Upright and mounding plant habit.
2. Dark green-colored foliage.
3. Freely branching growth habit.
4. Freely flowering habit.

5. Red purple-colored flowers.
6. Large glossy red-colored fruits.
7. Good garden performance.

Plants of the new Rose differ from plants of the female parent selection primarily in plant size as plants of the new Rose are shorter than plants of the female parent selection.

Plants of the new Rose differ from plants of the male parent selection primarily in flowering habit as plants of the new Rose are more freely flowering than plants of the male parent selection.

Plants of the new Rose can be compared to plants of the *Rosa hybrida* 'Meipopul', disclosed in U.S. Plant Pat. No. 9,777. Plants of the new Rose differ from plants of 'Meipopul' in the following characteristics:

1. Plants of the new Rose are more freely flowering than plants of 'Meipopul'.
2. Fruits of plants of the new Rose are glossier than fruits of plants of 'Meipopul'.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose.

The photograph at the bottom of the sheet comprises a side perspective view of a typical flowering and fruiting plant of 'Bokrammi' ground in an outdoor nursery.

The photograph at the top of the sheet is a close-up view of typical flowers of 'Bokrammi'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown during the summer in Boskoop, The Netherlands, in an outdoor nursery and under commercial production practices. During the production of the plants, day temperatures ranged from 14° C. to 32° C. and night temperatures ranged from 7° C. to 14° C. Plants had been growing for years when the photographs and description were taken. In the following description, color references are made to The Royal Horticultural Society Colour Chart, 2001 Edition, except where general terms of ordinary dictionary significance are used.

Botanical classification: *Rosa hybrida* 'Bokrammi'.

Parentage:

*Female, or seed, parent.*—Unnamed seedling selection of *Rosa hybrida,* not patented.

*Male, or pollen, parent.*—Unnamed seedling selection of *Rosa hybrida,* not patented.

Propagation:

*Type.*—Softwood cuttings.

*Time to initiate roots.*—About four weeks at 22° C.

*Time to produce a rooted young plant.*—About three months at 18° C.

*Root description.*—Thin; brown in color.

Plant description:

*Plant form.*—Upright and mounding perennial shrub.

*Growth habit.*—Moderately vigorous growth habit.

*Branching habit.*—Freely basal branching habit; dense and bushy growth habit.

*Plant height.*—About 68 cm.

*Plant width* (*spread*).—About 87 cm.

*Lateral branches.*—Length: About 14.5 cm. Diameter: About 5 mm. Internode length: About 3.1 cm. Strength: Strong. Texture: Smooth, glabrous. Color: Close to 144A. Thorns: Quantity: About one per 7 cm of stem. Shape: Triangular with sharp acuminate apices. Height: About 9 mm. Diameter, at base: About 7 mm. Color: Close to 173A to 173C.

Foliage description:

*Arrangement.*—Alternate; pinnately compound with about five or seven leaflets per leaf.

*Leaf length.*—About 12.8 cm.

*Leaf width.*—About 8.6 cm.

*Leaflet length.*—About 4.9 cm.

*Leaflet width.*—About 3.2 cm.

*Leaflet shape.*—Ovate.

*Leaflet apex.*—Acute.

*Leaflet base.*—Obtuse.

*Leaflet margin.*—Serrate.

*Leaflet texture, upper and lower surfaces.*—Smooth, glabrous.

*Leaflet luster, upper and lower surfaces.*—Glossy.

*Leaflet venation pattern.*—Pinnate.

*Leaflet color.*—Developing leaflets, upper surface: Close to 144A. Developing leaflets, lower surface: Close to 146C. Fully expanded leaflets, upper surface: Between 139A and 147A; venation, close to 147B. Fully expanded leaflets, lower surface: Close to 137C; venation, close to 144C.

*Leaf petiole.*—Length: About 2.4 cm. Diameter: About 1.5 mm. Texture, upper and lower surfaces: Smooth, glabrous. Color, upper and lower surfaces: Close to 144A to 144B.

Flower description:

*Flower type and habit.*—Rotate flowers arranged in compound corymbs with about 85 flowers per inflorescence. Flowers face mostly upright or slightly outwardly.

*Natural flowering season.*—Plants flower in the landscape from June through August in The Netherlands; flowers not persistent.

*Postproduction longevity.*—Flowers typically last about three days the plant. Cut stems with fruits last about two weeks.

*Fragrance.*—Slightly fragrant; typical of *Rosa;* sweet, pleasant.

*Flower buds.*—Height: About 1.6 cm. Diameter: About 1 cm. Shape: Ovoid. Color: Close to 60A.

*Inflorescence height.*—About 21 cm.

*Inflorescence diameter.*—About 32 cm.

*Flower diameter.*—About 3.9 cm.

*Flower depth.*—About 3.4 cm.

*Petals.*—Quantity per flower: About seven. Length: About 2.5 cm. Width: About 2.4 cm. Shape: Broadly obcordate. Apex: Retuse. Base: Attenuate. Margin: Entire. Texture, upper and lower surfaces: Smooth, glabrous. Color: Developing petals, upper surface: Close to N57A; towards the base, close to N57D. Developing petals, lower surface: Close to 58B; towards the base, close to 58D. Fully expanded petals, upper and lower surfaces: Close to 61C; towards the base, close to 62D. With development, color becoming closer to between 61A and 61C.

*Sepals.*—Quantity per flower: Five. Length: About 2 cm. Width: About 7 mm. Shape: Narrowly ovate. Apex: Acuminate. Base: Broadly cuneate. Margin: Entire. Texture, upper and lower surfaces: Smooth, glabrous. Color: Developing and fully expanded sepals, upper surface: Close to 144B; towards the margins, close to 144D. Developing and fully expanded, lower surface: Close to 146A; towards the margins, close to 144A to 144B.

*Peduncles.*—Length: About 10.7 cm. Diameter: About 3 mm. Orientation: About 50° from vertical. Strength: Strong. Color: Close to 144A.

*Pedicels.*—Length: About 2.3 cm. Diameter: About 1.5 mm. Orientation: About 45° from vertical. Strength: Strong. Color: Close to 144A tinged with close to 178A to 178B.

*Reproductive organs.*—Stamens: Quantity per flower: Numerous, about 50. Anther shape: Oblong. Anther length: About 2 mm. Anther color: Close to N199D. Pollen amount: Scarce. Pollen color: Close to 13A. Pistils: Quantity per flower: About 15. Pistil length: About 3 mm. Stigma shape: Irregularly flattened. Stigma color: Close to 152C. Style length: About 2.5 mm. Style color: Close to 151A to 151B. Ovary color: Close to 146A to 146B.

*Fruits.*—Quantity per flower: One. Length: About 1.7 cm. Diameter: About 1.1 cm. Texture: Smooth, glabrous. Luster: Glossy. Color: Close to 42A to 42B; towards the base, close to 31A.

*Seeds.*—Quantity per fruit: About 20. Length: About 4 mm. Diameter: About 3 mm. Color: Close to 164D.

Pathogen/pest resistance: Plants of the new Rose have been observed to be resistant to Black Spot and Powdery Mildew. Plants of the new Rose have not been observed to be resistant to pests and other pathogens common to Roses.

Garden performance: Plants of the new Rose have been observed have good garden performance and to tolerate rain, wind and temperatures ranging from about −20° C. to about 35° C.

It is claimed:

1. A new and distinct Rose plant named 'Bokrammi' as illustrated and described.

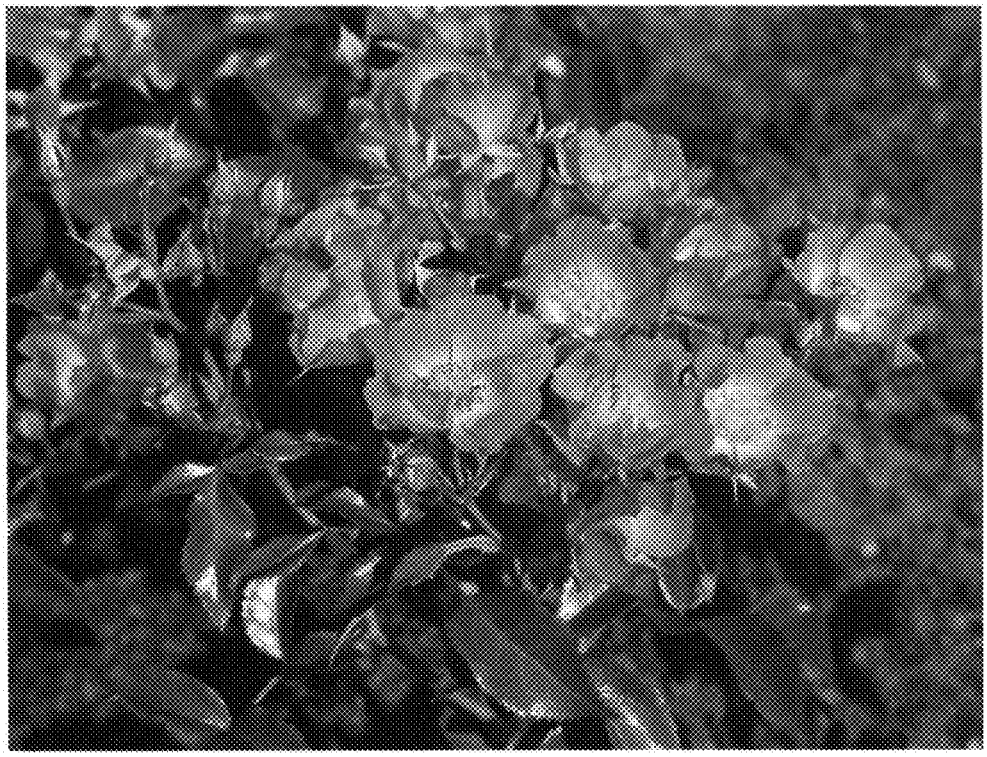
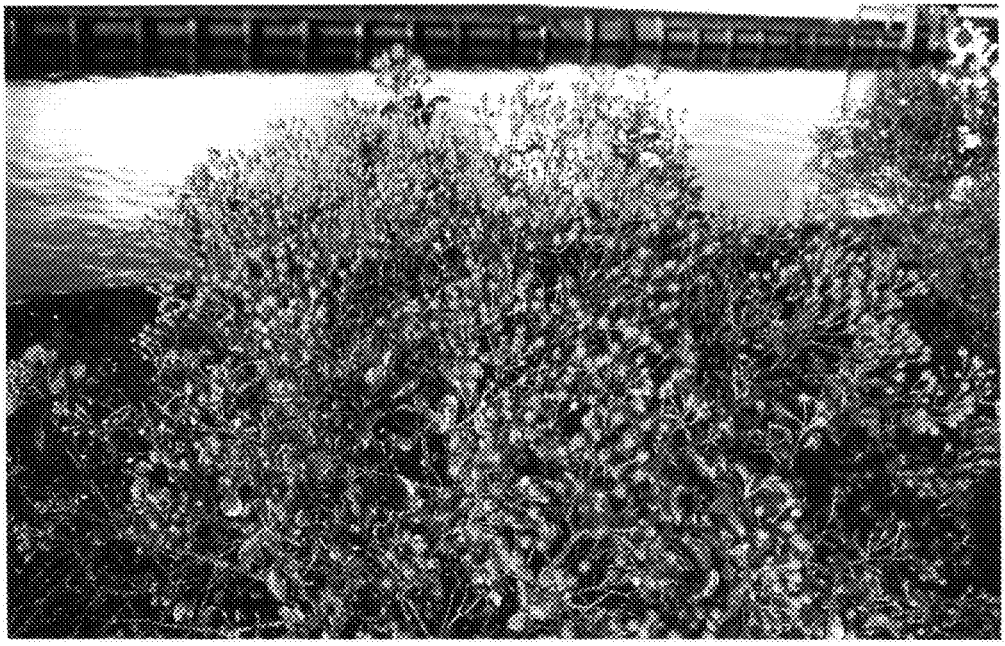

* * * * *